United States Patent [19]
Nakajima et al.

[11] Patent Number: 6,063,382
[45] Date of Patent: May 16, 2000

[54] BACTERIOSTATIC AND ANTIBACTERIAL AGENT CONTAINING MANGO KERNEL COMPONENT

[75] Inventors: Hadjime Nakajima; Seiichiro Tadokoro; Honoo Hashiba; Fumio Ito; Hirokazu Furuya; Toshihide Kabuki; Megumi Arai; Shunichi Dosako, all of Saitama, Japan

[73] Assignee: Snow Brand Milk Products Co., Ltd., Hokkaido, Japan

[21] Appl. No.: 09/048,613

[22] Filed: Mar. 26, 1998

[30] Foreign Application Priority Data

Mar. 26, 1997 [JP] Japan .................................... 9-072924
Mar. 25, 1998 [JP] Japan .................................... 10-077971

[51] Int. Cl.[7] .................................................. A01N 65/00
[52] U.S. Cl. ............................................... 424/195.1
[58] Field of Search .......................................... 424/195.1

[56] References Cited

PUBLICATIONS

Computer Abstract FSTA 90(04):P0097 Parmar et al "Effect of mango seed kernels pre–extract on the oxidative stability of ghee" Food Chemistry (1990) 35 (2) 99–107.

Computer Abstract SCISEARCH 97:154302 Raman et al "Extraction, charcterisation and antimicrobial activites of mango see oil" Asian Jour. Chem. (Apr.–Jun. 1997) vol. 9 No. 2. pp 321–323.

Computer Abstract BIOSIS 97:35817 BIOBUSINESS Arogba "Physical, chemical and functional properties of Nigerian mango kernel and its processed flour" J. Sci. Food and Agr (1997) 73 (3) pp 321–328.

Computer Abstract FSTA 97(03):j0028 Auratulain et al "Study of macro and micro nutrients in mango seed kernels" Sci Inter. (1996) 8 (1) pp 37–38, (Abstract) 1997.

Computer Abstract CAPLUS DN 122:30134 Gafur et al "Studies on the selectin of suitable solvent mixture for the extraction of mango seed lipids" Bang. J. Sci. Ind. Res. (1993) 28 (4), pp 100–109.

G. Lakshminarayana[2], et al., Jaocs, vol. 60, No. 1 (Jan. 1983), pp. 88–89, Varietal Variations in Content, Characteristics and Composition of Mango Seeds and Fat[1].

*Primary Examiner*—Herbert J. Lilling
*Attorney, Agent, or Firm*—Knobbe, Martens, Olson & Bear, LLP

[57] ABSTRACT

A mango kernel triturate or mango kernel extract has a bacteriostatic and antibacterial activity, and thus can be used in food products or cosmetics as a bacteriostatic and antibacterial agent. Furthermore, agents for preventing and treating acne or agents for preventing dental caries can be provided by adding said extract as an effective component.

1 Claim, 1 Drawing Sheet

BACTERIOSTATIC AND ANTIBACTERIAL AGENT CONTAINING MANGO KERNEL COMPONENT

BACKGROUND OF THE INVENTION

1. Field of the Invention

The present invention relates to a mango kernel triturate or a mango kernel extract, which has a bacteriostatic and antibacterial activity, and bacteriostatic and antibacterial agents containing them as an effective component. Furthermore, the present invention relates to beverages and foods to which said bacteriostatic and antibacterial agent is added. Furthermore, the present invention relates to cosmetics to which said bacteriostatic and antibacterial agent is added. Furthermore, the present invention relates to oral hygienic products to which said bacteriostatic and antibacterial agent is added.

2. Description of the Related Art

Conventionally, various types of methods such as (1) heating, (2) reducing moisture activity, (3) smoking, (4) fermentation, and (5) adding antibacterial agents have been used as means to prolong shelf-life. The addition of antibacterial agents to foods has been a particularly effective means to control microbial contamination. Thus, recently, antibacterial agents derived from natural substances as well as chemically synthesized antibacterial agents have been developed. These antibacterial agents derived from natural substances are referred to as preservatives or shelf-life extenders for which various antibacterial agents derived from the extracts of natural substances, such as the thick-stemmed bamboo (*Phyllostachy heterocycla* MITF), yucca, Japanese horseradish, garlic and tea, have been used (Shokuhin to Kaihatsu, Vol. 30, pp. 27–33, 1996; Monthly Food Chemicals, August 1996).

On the other hand, a plant mango (Mangifera indica), which belongs to family Anacardiaceae, order Rutales, is grown naturally or cultivated mainly in tropical and sub-tropical regions. The fruit of the mango tree is used for food. For example, about 9,000 metric tons of the fruit were imported to Japan from January to September in 1996. Further, the oil extracted from mango kernels has been used as a cocoa butter substitute in countries such as India, and the oil cakes obtained after extraction and pressing processes have been used, for example, as a food filler (JAOCS, Vol. 60, p. 88, 1983).

SUMMARY OF THE INVENTION

In the course of intensive study to search for new substances derived from natural substances having bacteriostatic and antibacterial effects, the present inventors found that a mango kernel extract has a remarkable bacteriostatic and antibacterial effect. Moreover, the present inventors found that the mango kernel extract having this bacteriostatic and antibacterial effect can be used as a bacteriostatic and antibacterial agent for beverages and food products, and thus completed the present invention. Accordingly, one objective of the present invention is to provide a bacteriostatic and antibacterial agent: including components of a mango kernel as an effective component. Another objective of the present invention is to provide beverages, food products and cosmetics to which the bacteriostatic and antibacterial agent including components of the mango kernel as an effective component is added.

A further objective of the present invention is to provide cosmetics for preventing or treating acne to which the bacteriostatic and antibacterial agent having the mango kernel extract as an effective component is added. A still further objective of the present invention is to provide oral hygienic products for preventing dental caries to which the bacteriostatic and antibacterial agent having the mango kernel extract as an effective component is added.

The bacteriostatic and antibacterial agent of the present invention contains a component of the kernels of edible mangos having bacteriostatic and antibacterial effects, as an effective component. This component shows considerable bacteriostatic and antibacterial effects on eukaryote microorganisms and prokaryotic organisms; thus, it can be added to beverages and food products or cosmetics to improve their shelf life.

Further, since the bacteriostatic and antibacterial agent of the present invention has an excellent antibacterial effect on *Propionibacterium acnes*, which is a causative agent of acne and axillary odor, it can be used in cosmetics for preventing and treating acne in various forms such as a bathing agent, emulsion, cosmetic cream and soap.

Furthermore, since the bacteriostatic and antibacterial agent of the present invention also has an excellent antibacterial effect on *Streptococcus sanguis*, which is a causative agent of dental caries, it can be used in beverages and food products for preventing dental caries or oral hygienic products for preventing dental caries.

DETAILED DESCRIPTION OF THE INVENTION AND PREFERRED EMBODIMENTS

Figure 1:
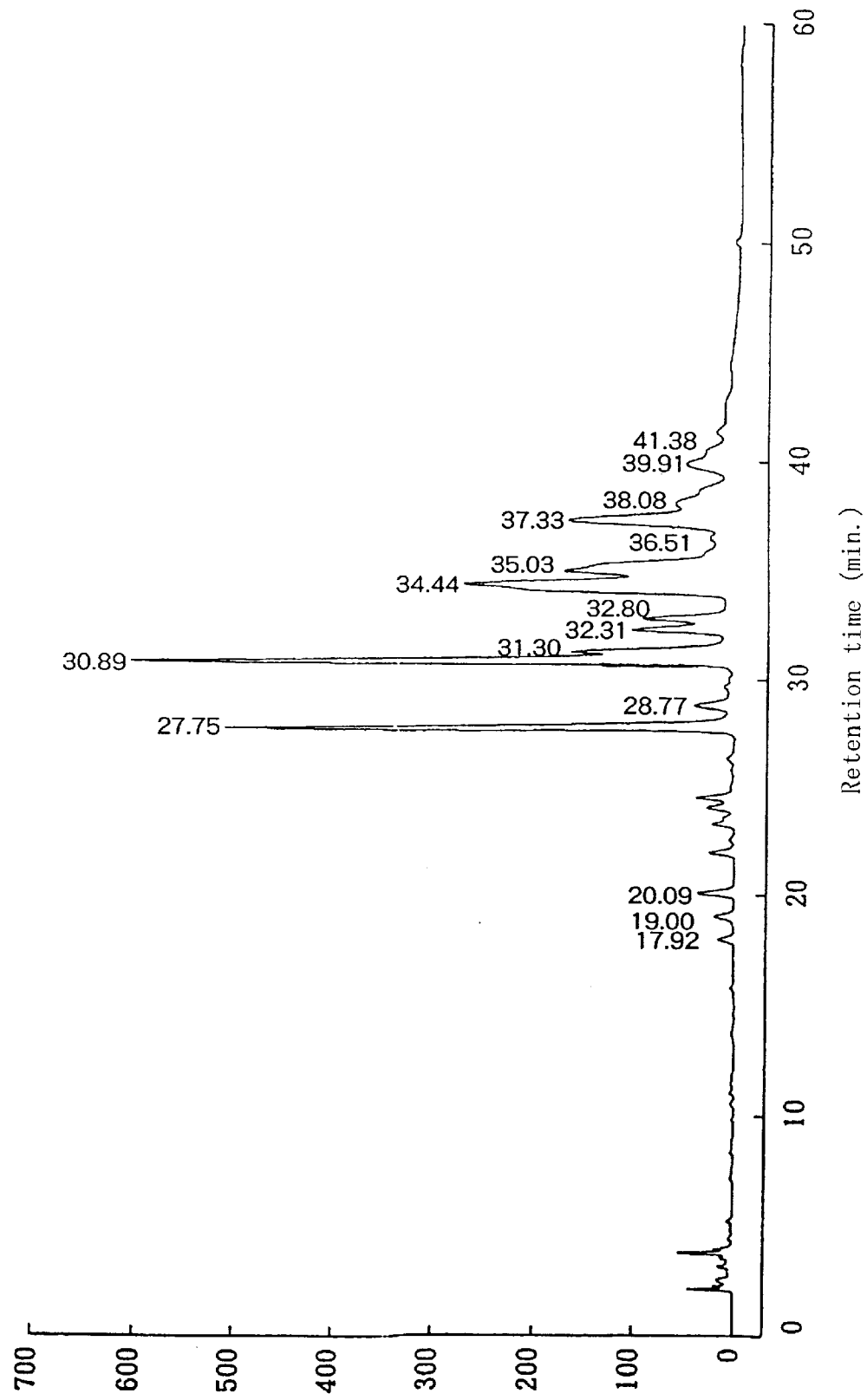
FIG. 1 shows a chromatograph of a mango kernel extract.

The bacteriostatic and antibacterial agent of the present invention contains a mango kernel triturate or a mango kernel extract as an effective component. Further, the mango kernel triturate or the mango kernel extract can be used by itself as a bacteriostatic and antibacterial agent. The bacteriostatic and antibacterial agent of the present invention can be provided in the form of a composition in which it is combined with a carrier, base, diluent, or the like selected as a function of intended usage. An organic acid, antioxidant, pH controlling agent, emulsifier, or the like can also be added to the bacteriostatic and antibacterial agent of the present invention.

The mango kernel triturate can be easily obtained by removing shells from seeds picked up form mangos to obtain mango kernels and grinding the mango kernels in a conventional grinder such as a homogenizer generally used. Particle size of the mango kernel triturate are not specially restricted. It is preferable to grind kernels to particles of a diameter size of 2 mm or less than 2 mm. The lower limit of the particle size is also not restricted. Mango kernels may be ground to a powder having a particle size of about 0.1 $\mu$m by a conventional grinding machine to produce powder. Particles having the particle size of 2 mm are sufficient for preparation of the mango kernel extract.

The mango kernel extract can be produced by contacting mango kernel triturate with a solvent for extraction to obtain an extract solution composed of the solvent and components which have a bacteriostatic and antibacterial activity extracted form the mango kernel triturate. After insoluble materials are removed by filter filtration if necessary, the solvent is removed from the extract solution by a process suitable for removal of the solvent. The residue thus obtained can be used as the mango kernel extract for an effective ingredient of a bacteriostatic and antibacterial agent.

As the solvent for extraction, organic solvents such as ethanol, methanol, isopropanol and diethyl sulfoxide (DMSO); and water or hot water which may contain salt(s) can be used.

Extraction temperature may be selected the properties of the solvent. The extraction may carried out at a temperature from 4° C. to 100° C. Since the extracted components having a bacteriostatic and antibacterial activity according to the present invention has thermal resistance, the solvent may be removed by heating. When volatile solvent is used for extraction, vacuum drying using, for example, a rotary evaporator.

The appearance of the extract as an residue may vary according to the solvent. The extract may be solved or suspended in water for the desired uses. The extract solution, which is obtained by contacting mango kernels with a solvent and removing insoluble materials if required, may be used directly for the desired uses, if the solvent is suitable for the uses. The extract solution may be further concentrated or diluted for the desired uses.

When the extract solution or its concentrate or dilute solution is used, its amount may be selected based on the amount of a mango kernel extract in the form of the residue, i.e., regarding the amount of the extract solution corresponding to the residue form extract.

The mango kernel triturate or the mango kernel extract according to the present invention can be added to a broad range of beverages and food products; in particular, because of its excellent heat stability, it can be used in cooked food products which are kept at room temperature after heating, such as croquettes, gratin, dumplings stuffed with minced pork, hamburgers, potatoes with minced meat, and minced beef with tofu. Further, it can be used in food products which are baked or boiled in the final process, such as bread, pizza crust, and noodles. Further, it can be used in desserts having a mango flavor, such as juices, jellies, yogurt and mousse. The color of the mango kernel extract is liver-brown, thus coloring may occur when added to food products at a concentration of more than 2%, but in such cases, it can still be blended into supplementary materials, such as soy sauce and Worcester sauce. The bacteriostatic and antibacterial agent of the present invention is preferably added to beverages and food products so that a mango kernel trirurate or a mango kernel extract in the form of residue is present at a concentration between 10 ppm and 50,000 ppm in beverages and food products.

Addition of this mango kernel triturate or mango kernel extract having bacteriostatic and antibacterial activity into beverages and food products can suppress an increase in general bacterial counts in the beverages and food products and can extend their shelf life.

Further, beverages and food products supplemented with the mango kernel triturate or mango kernel extract can be used as beverages and food products for the prevention of dental caries or oral hygienic products for the prevention of dental caries.

The mango kernel triturate or the mango kernel extract can be used as a component of either a bacteriostatic and antibacterial agent or a preservative to improve stability in preservation of cosmetics including bathing agents and medicines. The amount for such uses may vary in a wide range which can be provides the bacteriostatic and antibacterial activity and which does not reduce the desired effects of the cosmetics and medicines. The amounts may range preferably between 10 ppm to 50,000 ppm. When the extract solution or its concentrate or dilute is used the amount to be added can be converted form that of its residue form.

An anti-acne agent can be prepared by using a mango kernel triturate or a mango kernel extract as an effective ingredient. An effective amount, for example, 10 ppm to 50000 ppm of the mango kernel triturate or the mango kernel extract as the residue form may be mixed with a base, a carrier or a diluent for pharmaceutical uses to obtain a composition.

The pharmaceutically acceptable bases, carriers and diluents include for example, vaseline, plastibases and liquid paraffin.

A mango kernel triturate or a mango kernel extract can be combined with a cosmetic base to provide cosmetics for cleansing or basic cosmetics such as creams, emulsions, make-up creams, cosmetic oils and packs, as cosmetic compositions to which an anti-acne activity is additionally added.

In producing cosmetics, various known cosmetic bases, such as excipients, binding agents, lubricants and disintegrating agents, can be used, if necessary.

The amount of the mango kernel triturate or the mango kernel extract in cosmetics varies depending on the form of the formulations and cannot be generalized and not particularly limited; however, at least one of the mango kernel triturate and mango kernel extract as the residue form should be generally included in the range of about 0.1–10% by weight, preferably about 0.2–5% by weight. Furthermore, the abovementioned cosmetics can be diluted with water, ethanol, olive oil or appropriate solvents.

Oral hygienic products can be also produced by using a mango kernel triturate or a mango kernel extract according to conventional processes. The oral hygienic products include tooth pastes and mouth washes, oral refreshment, troches and chewing gum. The amount of the mango kernel triturate or the mango kernel extract as the residue form may vary in the range from 10 ppm to 50,000 ppm. Other pharmatical agents can be added to the oral hygienic products if required.

The present invention will be explained more in detail by following Examples and Test Examples. In the following examples, "%" means "wt. %".

EXAMPLE 1

Preparation of a mango kernel extract

Kernels (53 g) removed from mangos produced in Australia were triturated using a homogenizer (NISSEI, AM-3) at 150 rpm for 5 minutes, 200 ml of ethanol were added, and extraction was carried out in a cold and dark place overnight while shaking. The resulting ethanol extract solution was filtered through a filter paper to remove insoluble substances, then the filtrate was dried to a solid under vacuum in a rotary evaporator to obtain 10.1 g of a mango kernel extract.

This extract was analyzed by reversed phase chromatography using a HPLC system of Hewlett Packard 1050 System. Results are shown in FIG. 1. Conditions for the reversed phase chromatography were as follows:

Column: TSK gel ODS-120T, 4.6×150 mm, Toso Corp.

Solvent: water and acetonitrile

Amount of samples injected: 10.00 μl (dilution ratio=1:1)
Pump flow rate: 1,000 ml/min
Measured wave length: 280 nm
Pump time program: Shown in Table 1

TABLE 1

| No. | Time (minutes) | Flow rate (ml/min) | Water(%) | Aceetonitrile(%) |
|---|---|---|---|---|
| | Initiate value | 1.000 | 90.0 | 10.0 |
| 1 | 45.00 | 1.000 | 70.0 | 30.0 |
| 2 | 50.00 | 1.000 | 10.0 | 90.0 |
| 3 | 55.00 | 1.000 | 10.0 | 90.0 |

Antibacterial activity of each fraction fractionated by the reverse chromatography was tested according to the procedure as described in Test example 1 by adding each fraction into an agar plate, streaking *Escherichia coli* IFO-3301 cells onto each agar plate, incubating each plate at an optimum temperature and determining the activity based on bacterial growth. As a result, Antibacterial activity was observed in the fractions having retention times of 30.89, 31.30, 34.44 and 35.03 minutes.

TEST EXAMPLE 1

Minimum growth inhibition concentrations (MICs) of the mango kernel extract obtained in Example 1 were determined for various bacteria. The mango kernel extract was diluted with distilled water to prepare a series of diluted solutions having designated concentrations, then a standard agar medium (Pearlcoa Standard Agar Medium, a product of Eiken Chemical Co., Ltd.) was added to each diluted solution to obtain a series of agar media containing mango kernel extract. A suspension of about 1×10$^8$ cfu/ml of each bacterial strain was streaked onto each agar medium using a sterilized platinium wire, and incubation was carried out under the optimum conditions for each bacteria. The minimum concentrations of diluted solutions in which no bacterial growth was first observed after 1 day incubation were set as MICs. Results are shown in Table 2.

TABLE 2

| Bacterial strain | MIC (ppm) |
|---|---|
| *Bacillus cereus* IFO-14160 | 125 |
| *Bacillus subtilis* IFO-13719 | 250 |
| *Escherichia coli* IFO-3301 | 75 |
| *Salmonella typhimurium* ATCC-13311 | 75 |
| *Pseudomonas aeruginosa* ATCC-27853 | 75 |
| *Pseudomonas fluorescens* IFO-14160 | 125 |

Since MICs for antibacterial agents derived from natural products are generally at a level of several hundred ppm, it can be concluded that the mango kernel extract has excellent antibacterial effect.

TEST EXAMPLE 2

The heat stability of the mango kernel extract obtained in Example 1 was determined. For this, the mango kernel extract was heated at 121 C. for 15 minutes or 1 hour, then MICs for *Bacillus cereus* IFO-14160 were determined. Results are shown in Table 3.

TABLE 3

| Condition | MIC (ppm) |
|---|---|
| Unheated | 125 |
| 121° C., 15 minutes | 125 |
| 121° C., 1 hour | 500 |

From these results, it can be concluded that the antibacterial effect of the mango kernel extract is stable when heated at 121 C. for 15 minutes.

EXAMPLE 2

Preparation of a creamed corn gratin

A creamed corn gratin was prepared from 7.5% flour, 6% onion, 30% corn, 7% condensed milk, 8% butter, 1% sugar, 0.5% salt, 1% of the bacteriostatic and antibacterial agent containing the mango kernel extract obtained in Example 1, and 39% water, according to a conventional method.

Forced decomposition tests were carried out using this creamed corn gratin. The creamed corn gratin was stored at 30° C. to induce decomposition and the extent of putrefaction with the passage of time was observed. As a control, a creamed corn gratin was prepared from 7.5% flour, 6% onion, 30% corn, 7% condensed milk, 8% butter, 1% sugar, 0.5% salt, and 40% water and the same test for the forced decomposition was carried out. Results are shown in Table 4.

TABLE 4

| Storage time (days) | Product with bacteriostatic/ antibacterial agent | Product without bacteriostatic/ antibacterial agent |
|---|---|---|
| 0 | Normal | Normal |
| 1 | Normal | Slight putrid smell |
| 2 | Normal | Putrid smell |
| 3 | Normal | Putrid smell |
| 5 | Slightly putrid smell | — |

Thus, the addition of the mango kernel extract as a bacteriostatic and antibacterial agent in this manner can markedly improve the shelf life of the creamed corn gratin.

EXAMPLE 3

Preparation of a thick backed omelet

An egg solution was prepared from 73% whole egg, 0.9% light soy sauce, 0.3% salt, 2.5% sugar and 23.4% soup stock, supplemented with 0.5% or 2.0% of the mango kernel extract obtained in Example 1, and then baked in a frying pan to make a thick baked omelet. The composition of the egg solution was adjusted with the soup stock. The thick baked omelets thus made had a pale liver-brown color when 2.0% of the mango kernel extract was added; however, the color did not spoil palatability. The weight decreased by about 30% upon baking.

The thick baked omelets were stored at 30° C. for a forced decomposition and the extent of putrefaction with the passage of time was observed. A thick baked omelet without the supplement of the mango kernel extract was prepared and similarly tested as a control. Results are shown in Table 5.

TABLE 5

| Days of storage | With no supplement | With 0.5% supplement | With 2% supplement |
|---|---|---|---|
| 1 | Normal | Normal | Normal |
| 2 | Slight putrid smell | Normal | Normal |
| 3 | Putrid smell | Slight putrid smell | Normal |
| 4 | Petrified | Putrid smell | Normal |

Thus, the addition of the mango kernel extract as a bacteriostatic and antibacterial agent in this manner can markedly improve the shelf life of the thick baked omelets.

In addition, general bacterial counts in the thick baked omelets during storage were determined. Results are shown in Table 6.

TABLE 6

| Days of storage | With no supplement (cfu/g) | With 0.5% supplement (cfu/g) | With 2% supplement (cfu/g) |
|---|---|---|---|
| 1 | $7.6 \times 10^7$ | $1.7 \times 10^7$ | $<10^3$ |
| 2 | $2.0 \times 10^9$ | $4.8 \times 10^8$ | $<10^3$ |

Thus, the addition of the mango kernel extract as a bacteriostatic and antibacterial agent can suppress an increase in general bacterial counts in the thick baked omelet.

EXAMPLE 4

Preparation of a potato salad

A salad was prepared from 15% mashed potato, 10% carrot, 14.3% cucumber, 5.7% onion, 9.2% mayonnaise and 0.4% salt, supplemented with 0.5% or 2.0% of the mango kernel extract. For the mashed potato, mashed potato flakes were reconstituted by adding lukewarm water so as to adjust the abovementioned composition to a total of 100%. Carrots and onions were cut into an appropriate size, and then blanched in boiling water for one minute.

The potato salad samples were stored at 30° C. for forced decomposition and the extent of putrefaction with the passage of time was observed. As a control, a potato salad sample without the supplement of the mango kernel extract was prepared and similarly tested as a control. Results are shown in Table 7.

TABLE 7

| Days of storage | With no supplement | With 0.5% supplement | With 2% supplement |
|---|---|---|---|
| 1 | Normal | Normal | Normal |
| 2 | Putrid smell (slime) | Slight putrid smell | Normal |
| 3 | Putrid smell (fungi) | Putrid smell (fungi) | Slight putrid smell |

Thus, the addition of the mango kernel extract as a bacteriostatic and antibacterial agent in this manner can improve the shelf life of potato salad.

In addition, general bacterial counts in the potato salad samples during storage were determined. Results are shown in Table 8.

TABLE 8

| Days of storage | With no supplement (cfu/g) | With 0.5% supplement (cfu/g) | With 2% supplement (cfu/g) |
|---|---|---|---|
| 1 | $3.5 \times 10^8$ | $7.0 \times 10^4$ | $<10^3$ |
| 2 | $1.5 \times 10^9$ | $7.0 \times 10^8$ | $3.4 \times 10^5$ |

Thus, the addition of the mango kernel extract as a bacteriostatic and antibacterial agent can suppress an increase in general bacterial counts in potato salad.

TEST EXAMPLE 3

Minimum growth inhibition concentrations (MICs) of the mango kernel extract obtained in Example 1 were determined for various bacteria. Portions of appropriately diluted solutions of the mango kernel extract were dispensed into petri dishes, then GAM agar medium (a product of Nissui Pharmaceutical Co., Ltd.) was added to prepare test agar media. Test bacteria, which had been statically cultured in GAM media at 37° C. overnight, were diluted to a 1/100 ratio with GAM medium and streaked onto the agar media. The petri dishes were placed in an anaerobic culture jar, and then Anaeropack (a product of Mitsubishi Gas Chemical Co., Inc.) was placed inside the jar to provide an anaerobic atmosphere. Growth of the streaked test bacteria was observed after incubating at 37° C. for 2 days. The minimum concentrations of diluted solutions with no bacterial growth were set as the MICs. Results are shown in Table 9.

MIC for Propionibacterium acnes JCM-6425, which is a causative agent of acne and axillary odor, was 30 ppm, which suggested that the bacteriostatic and antibacterial agent of the present invention had an extremely good antibacterial effect.

Since MIC for Streptococcus sanguis JCM-5708, which is one of the causative agents of dental caries, was 250 ppm, the bacteriostatic and antibacterial effects of the mango kernel extracts were confirmed.

TABLE 9

| Bacterial strain | MIC (ppm) |
|---|---|
| Propionibacterium acnes JCM-6425 | 30 |
| Streptococcus sanguis JCM-5708 | 250 |

When the mango kernel extract is used in beverages and food products, it can suppress an increase in general bacterial counts, and thus improve the shelf life of the beverages and food products.

EXAMPLE 5

Chewing gum for preventing dental caries

A gum base was dissolved in a composition shown in Table 10. All the ingredients were blended and stirred and formed into chewing gum for preventing dental caries.

TABLE 10

| Component | Composition (%) |
|---|---|
| Gum base | 20.0 |
| Corn syrup | 9.0 |
| Dextrose monohaydrate | 10.0 |

TABLE 10-continued

| Component | Composition (%) |
|---|---|
| Lactose | 5.0 |
| Glycerine | 5.0 |
| Sugar | 50.0 |
| Mango kernel extract | 1.0 |

EXAMPLE 6

Ice cream for preventing dental caries

An ice cream mix was prepared with the ingredients shown in Table 11, and then an ice cream for preventing dental caries was produced according to a conventional method for manufacturing ice cream.

TABLE 11

| Component | Composition (%) |
|---|---|
| Cream (fat: 50%) | 17.0 |
| Cow's milk (fat: 3.7%) | 42.0 |
| Unsweetened condensed skim milk | 25.0 |
| Sugar | 11.2 |
| Corn syrup | 4.0 |
| Stabilizer | 0.3 |
| Mango kernel extract | 0.5 |

EXAMPLE 7

Bathing agent for preventing and treating acne

DL-sodium lactate (21 parts by wight), sodium pyruvate (8 parts by weight), the mango kernel extract obtained in Example 1 (10 parts by weight) and ethanol (35 parts by weight) were mixed with 26 parts by weight of purified water and a coloring agent and perfume in appropriate amounts to prepare a bathing agent. This product can be used in hot water for bathing at a dilution ranging from 100 to 10,000 times and is effective in preventing skin infection from the bacteria which cause acne.

EXAMPLE 8

Emulsion for preventing and treating acne

Polyoxyethylenebehenyl ether (0.5 part by wight), polyoxyethylenesorbitol tetraoleate (1 part by weight), lipophilic glycerine monostearate (1 part by weight) pyruvic acid (0.5 part by weight), behenyl alcohol (0.5 part by weight), avocado oil (1 part by weight), the mango kernel extract obtained in Example 1 (1 part by weight) and Vitamin E in an appropriate amount were dissolved while heating according to a conventional method, and then L-sodium lactate (1 part by weight), 1,3-butylene glycol (5 parts by weight), carboxyvinyl polymer (0.1 part by weight) and purified water (85.3 parts by weight) were added. The admixture was emulsified using a homogenizer, and further mixed and stirred while adding an appropriate amount of perfume to prepare an emulsion. This product is effective for prevention of skin infection with bacteria which cause acne.

EXAMPLE 9

Soap for preventing and treating acne

A solid soap was prepared according to a conventional method using the ingredients shown in Table 12.

TABLE 12

| Component | Composition (g) |
|---|---|
| Soap base | 30.0 |
| Hydrogenated coconut oil | 50.0 |
| Glyceryl fatty acid sodium sulphate | |
| Glyceryl monostearate | 5.0 |
| Cetyl alcohol | 5.0 |
| Titanium dioxide | 0.5 |
| Zinc oxide | 0.5 |
| Mango kernel extract | 0.05 |
| Perfume, antioxidant and metal ion chelator | In proper quantity |

EXAMPLE 10

Production of mouthwash for preventing dental caries

A mouthwash for preventing dental caries was prepared by mixing the ingredients shown in Table 13.

TABLE 13

| Component | Composition (%) |
|---|---|
| Ethanol | 8.0 |
| Perfume | 1.0 |
| Sorbitol | 5.0 |
| Propylene glycol | 5.0 |
| Mango kernel extract | 3.0 |
| Distilled water | 78.0 |

EXAMPLE 11

Production of toothpaste for preventing dental caries

The ingredients shown in Table 14 were mixed and the resulting cream was filled into containers to produce a toothpaste for preventing dental caries.

TABLE 14

| Component | Composition (%) |
|---|---|
| Glycerine | 70.0 |
| Silicon dioxide | 20.0 |
| Xanthan gum | 1.0 |
| Mint flavor | 1.0 |
| Titanium dioxide | 0.7 |
| Sodium fluoride | 0.3 |
| Distilled water | 5.0 |
| Mango kernel extract | 2.0 |

What is claimed is:

1. A bacteriostatic and antibacterial composition comprising:
   a mango kernel extract extracted from mango kernels with a solvent selected from the group consisting of ethanol, methanol, isopropanol, and diethyl sulfoxide, in an amount of 10–50,000 ppm, as a residue after removing the solvent, as measured in a final product to which said composition is added to exhibit bacteriostatic and antibacterial activity; and
   an acceptable carrier.

* * * * *